US012168232B2

(12) United States Patent
Sun et al.

(10) Patent No.: US 12,168,232 B2
(45) Date of Patent: Dec. 17, 2024

(54) OPEN FLUIDIC ARRAY SYSTEMS AND METHODS OF MAKING AND USING SAME

(71) Applicant: Georgia Tech Research Corporation, Atlanta, GA (US)

(72) Inventors: Gongchen Sun, Atlanta, GA (US); Hang Lu, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 672 days.

(21) Appl. No.: 17/499,515

(22) Filed: Oct. 12, 2021

(65) Prior Publication Data
US 2022/0032290 A1 Feb. 3, 2022

Related U.S. Application Data

(63) Continuation of application No. 17/384,775, filed on Jul. 25, 2021, now abandoned.

(60) Provisional application No. 63/056,762, filed on Jul. 27, 2020.

(51) Int. Cl.
*B01L 3/00* (2006.01)

(52) U.S. Cl.
CPC ..... *B01L 3/5085* (2013.01); *B01L 2200/0642* (2013.01); *B01L 2200/12* (2013.01); *B01L 2300/161* (2013.01)

(58) Field of Classification Search
CPC ........ B01L 2200/0642; B01L 2200/12; B01L 2300/045; B01L 2300/0819; B01L 2300/161; B01L 3/0293; B01L 3/5085; B01L 3/50853; C12M 23/12
See application file for complete search history.

(56) References Cited

U.S. PATENT DOCUMENTS

2008/0102006 A1* 5/2008 Kram ..................... G01N 1/312
222/1

FOREIGN PATENT DOCUMENTS

EP          2143492 A1 *  1/2010  .......... B01J 19/0046
WO    WO-2016069885 A1 *  5/2016  .............. C12M 1/14

* cited by examiner

*Primary Examiner* — Jennifer Wecker
(74) *Attorney, Agent, or Firm* — Troutman Pepper Hamilton Sanders LLP; Ryan A. Schneider; Brandon M. Reed

(57) ABSTRACT

An exemplary embodiment of the present disclosure provides a fluidic device comprising a substrate, an applicator, and a spacer. The substrate can comprise a plurality of wells. The applicator can be used for manipulating a biological substance in at least a portion of the plurality of wells. The spacer can be positioned between the substrate and the applicator. The spacer can be configured to allow the applicator to apply the biological substance to at least a portion of the plurality of wells while maintaining a space between the substrate and the applicator.

14 Claims, 15 Drawing Sheets

OPEN FLUIDIC ARRAY SYSTEMS AND METHODS OF MAKING AND USING SAME

CROSS-REFERENCE TO RELATED APPLICATIONS

Figure 1A:
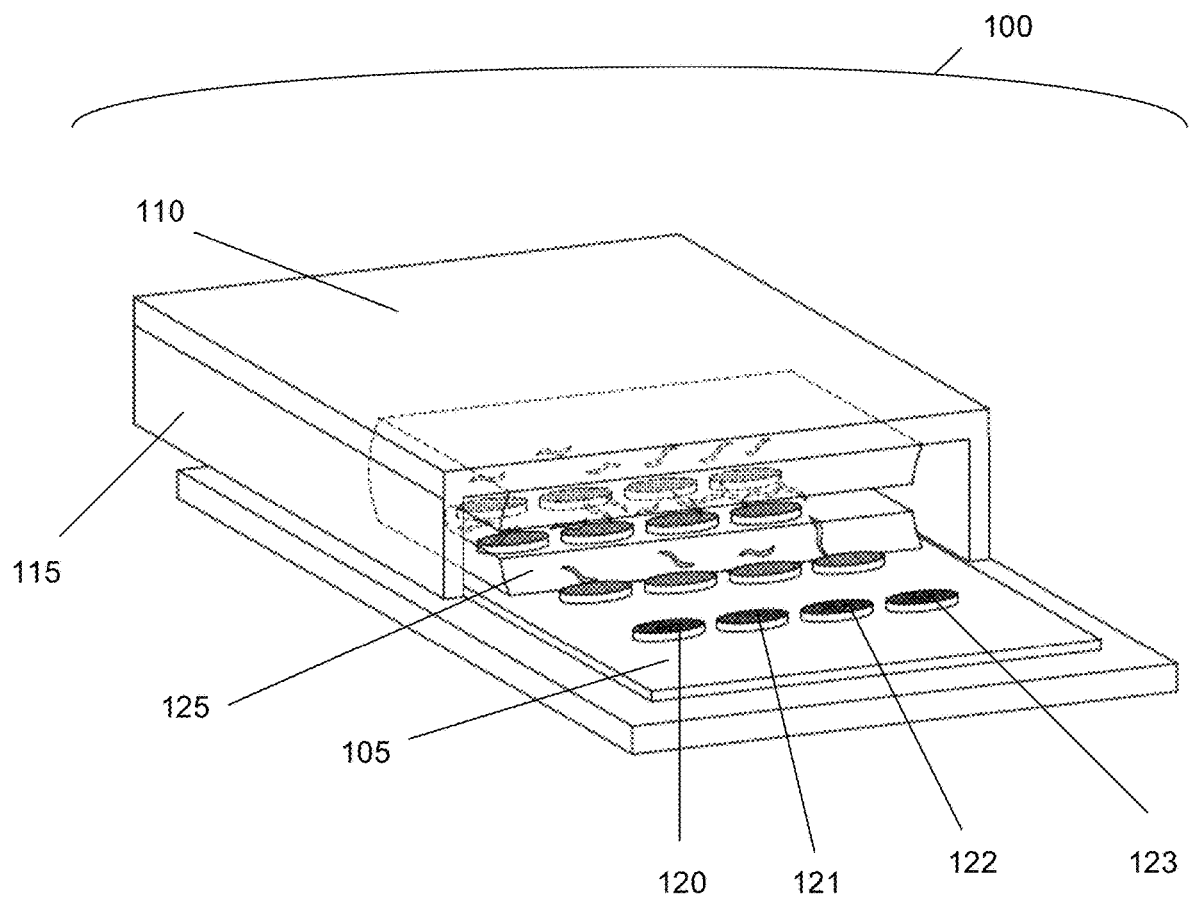

This application claims the benefit of U.S. patent application Ser. No. 17/384,775, filed on 25 Jul. 2021, and U.S. Provisional Application Ser. No. 63/056,762, filed on 27 Jul. 2020, which are incorporated herein by reference in their entireties as if fully set forth below.

GOVERNMENT LICENSE RIGHTS

This invention was made with government support under Agreement No. 1707401, awarded by National Science Foundation. The government has certain rights in the invention.

FIELD OF THE DISCLOSURE

The various embodiments of the present disclosure relate generally to fluidic systems for manipulating biological substances and methods of making and using same.

BACKGROUND

There are two major challenges of performing high-throughput biologics (including, but not limited to, cells, organisms, macromolecules, synthetic systems, and the like) level screening: one is to handle and rapidly isolate the biological entities; the other is to precisely control the microenvironment that stimulates or manipulates individual samples in an array/parallel fashions. Conventional fluidic devices have been developed in an attempt to meet these needs. Different closed-channel fluidic systems have been designed and coupled with automated microscopy to isolate biological substance in microchannels for high-resolution imaging or in microchambers for behavior analysis. Comprehensive forward genetic screening by image-based deep phenotyping and large-scale drug screening are hence made possible.

Despite demonstration of these applications, the adoption of these fluidic technologies into generic biology laboratories have been slow. This is primarily because different fluidic device designs are usually optimized for only one specific screening function, such as mutant sorting through high-resolution imaging of immobilized animals or freely moving behavioral analysis in response to chemical stimuli. Prototyping and fabricating a library of devices to perform different screening functions is time-consuming and can be expensive. Furthermore, conventional devices and methods have not been successful in adapting devices for screening biologics. The challenge is that these micro-swimmers usually have an irregular body shape and are highly mobile, which make them difficult to handle and isolate by conventional methods, such as droplet partitioning. These conventional microfluidic techniques, however, use either manual loading or stochastic sample sedimentation by gravity and mostly work only with static single cells. Accordingly, there is a need for improved open-surface microfluidic techniques. Embodiments of the present disclosure address this desire.

BRIEF SUMMARY

The present disclosure relates to open fluidic array systems for manipulating biological substances. An exemplary embodiment of the present disclosure provides an open fluidic array device. The fluidic device can comprise a substrate, an applicator, and a spacer. The substrate can comprise a plurality of wells. The applicator can be used for manipulating a biological substance in at least a portion of the plurality of wells. The spacer can be positioned between the substrate and the applicator. The spacer can be configured to allow the applicator to apply the biological substance to at least a portion of the plurality of wells while maintaining a space between the substrate and the applicator.

In any of the embodiments disclosed herein, the plurality of wells can be at least partially filled with a hydrophilic microgel.

In any of the embodiments disclosed herein, the substrate can comprise a hydrophobic material defining boundaries of the plurality of wells.

In any of the embodiments disclosed herein, the plurality of wells can be spaced apart in the substrate such that the following equation is satisfied, $$\frac{h}{d} < \left(1 - \frac{\cos\theta_{substrate}}{\cos\theta_{microgel}}\right)$$

wherein h can be a height of the space between the substrate and the applicator, d can be a distance between adjacent wells in the plurality of wells, $\theta_{microgel}$ can be a receding contact angle of the hydrophilic microgel, and $\theta_{substrate}$ can be a receding contact angle of the hydrophobic material.

In any of the embodiments disclosed herein, the spacer can be located on the applicator.

In any of the embodiments disclosed herein, the spacer can be located on the substrate.

In any of the embodiments disclosed herein, the spacer can comprise a first rail and a second rail. The first rail can extend along at least a portion of a top surface of the substrate. The second rail can extend along at least a portion of the top surface of the substrate. The second rail can substantially be parallel to the first rail.

Another exemplary embodiment of the present disclosure provides a method of making an open fluidic array device. The method can comprise: providing a substrate comprising a hydrophobic material; creating a plurality of wells in the substrate; providing an applicator for manipulating a biological substance in at least a portion of the plurality of wells; and providing a spacer configured to allow the applicator to apply the biological substance to the at least a portion of the plurality of wells while maintaining a space between the substrate and the applicator.

In any of the embodiments disclosed herein, the method can comprise filling the plurality of wells with a hydrophilic microgel.

In any of the embodiments disclosed herein, the plurality of wells with the hydrophilic microgel can comprise a dewetting process.

In any of the embodiments disclosed herein, the method can comprise gelating the hydrophilic microgel.

In any of the embodiments disclosed herein, the gelating can comprise exposing the hydrophilic microgel to ultraviolet light.

In any of the embodiments disclosed herein, creating the plurality of wells can result in the plurality of wells being spaced apart in the substrate such that the following equation is satisfied, $$\frac{h}{d} < \left(1 - \frac{\cos\theta_{substrate}}{\cos\theta_{microgel}}\right)$$

wherein h can be a height of the space between the substrate and the applicator, d can be a distance between adjacent wells in the plurality of wells, $\theta_{microgel}$ can be a receding contact angle of the hydrophilic microgel, and $\theta_{substrate}$ can be a receding contact angle of the hydrophobic material.

In any of the embodiments disclosed herein, creating the plurality of wells can comprise at least one of laser cutting the substrate, micro machining the substrate, or blade cutting the substrate.

In any of the embodiments disclosed herein, providing the spacer can comprise at least one of providing the spacer on the applicator and providing the spacer on the substrate.

Another exemplary embodiment of the present disclosure provides a method of manipulating a biological substance in an open fluidic array device. The method can comprise: providing the fluidic device; and applying the biological substance to the plurality of wells with an applicator. The fluidic device can comprise a substrate and a plurality of wells. The substrate can comprise a hydrophobic material. The plurality of wells can be located within the substrate. The plurality of wells can be filled with a hydrophilic microgel. The biological substance can be applied to the plurality of wells with an applicator while maintaining a space between a top surface of the substrate and a bottom surface of the applicator.

In any of the embodiments disclosed herein, applying the biological substance to the plurality of wells can comprise moving the applicator along the top surface of the substrate while maintaining the space between the top surface of the substrate and the bottom surface of the applicator.

In any of the embodiments disclosed herein, the space between the top surface of the substrate and the bottom surface of the applicator can be maintained by a spacer positioned between the top surface of the substrate and the bottom surface of the applicator.

In any of the embodiments disclosed herein, the space between the top surface of the substrate and the bottom surface of the applicator can satisfy the following equation, $$\frac{h}{d} < \left(1 - \frac{\cos\theta_{substrate}}{\cos\theta_{microgel}}\right)$$

wherein h can be a height of the space between the top surface of the substrate and the bottom surface of the applicator, d can be a distance between adjacent wells in the plurality of wells, $\theta_{microgel}$ can be a receding contact angle of the hydrophilic microgel, and $\theta_{substrate}$ can be a receding contact angle of the hydrophobic material.

Figure 5A:
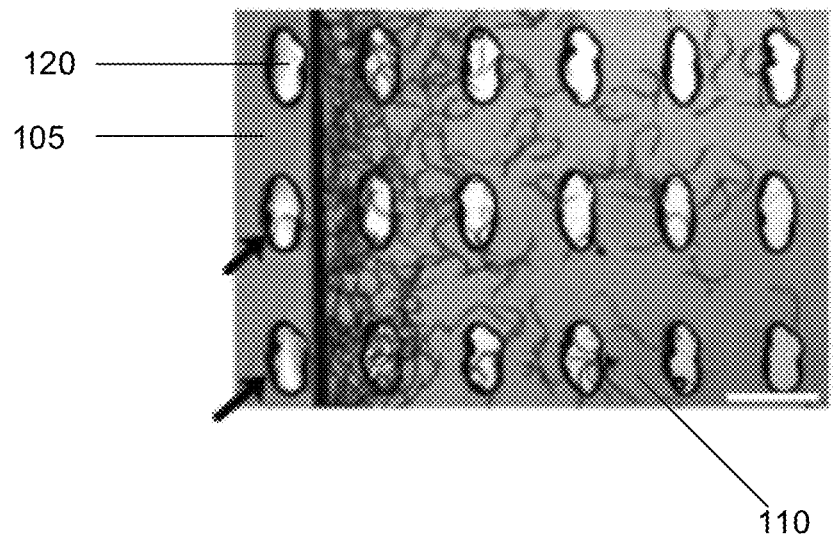

In any of the embodiments disclosed herein, moving the applicator along the top surface of the substrate can comprise moving the applicator along the top surface of the substrate at a predetermined speed. The predetermined speed can be calculated according to the following equation, $$t_c/t_{sliding} = Ca \; 3 \; l_g/\alpha h$$

wherein $t_c$ can be a local meniscus collapsing timescale, $t_{sliding}$ can be a biological substance sliding timescale, Ca can be a capillary number, $l_g$ can be a length of wells in the plurality of wells, and $\alpha$ can be calculated according to the following equation, $$\alpha = (\cos\theta_{microgel} - \cos\theta_{substrate}) - \frac{h}{d}\cos\theta_{microgel}$$

wherein h can be a height of the space between the top surface of the substrate and the bottom surface of the applicator, d can be a distance between adjacent wells in the plurality of wells, $\theta_{microgel}$ can be a receding contact angle of the hydrophilic microgel, and $\theta_{substrate}$ can be a receding contact angle of the hydrophobic material.

These and other aspects of the present disclosure are described in the Detailed Description below and the accompanying drawings. Other aspects and features of embodiments will become apparent to those of ordinary skill in the art upon reviewing the following description of specific, exemplary embodiments in concert with the drawings. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

FIG. 1A provides an illustration of an open fluidic array device, in accordance with an exemplary embodiment of the present disclosure.

FIG. 1B provides an illustration of an open fluidic array device with the spacer comprising of a first rail and a second rail, in accordance with an exemplary embodiment of the present disclosure.

FIG. 2A provides an illustration of the substrate, in accordance with an exemplary embodiment of the present disclosure.

FIG. 2B provides an illustration of the substrate from a top view, in accordance with an exemplary embodiment of the present disclosure.

FIG. 3A provides an illustration of the substrate during the creating of the plurality of wells, in accordance with an exemplary embodiment of the present disclosure.

FIG. 3B provides an image of the substrate, in accordance with an exemplary embodiment of the present disclosure.

FIG. 4A provides an illustration of the substrate with biological substance, in accordance with an exemplary embodiment of the present disclosure.

FIG. 4B provides an illustration of the substrate with biological substance after using the method of manipulating a biological substance in an open fluidic array device, in accordance with an exemplary embodiment of the present disclosure.

FIG. 5A provides an image of the substrate during the method of manipulating a biological substance in an open fluidic array device, in accordance with an exemplary embodiment of the present disclosure.

Figure 5B:
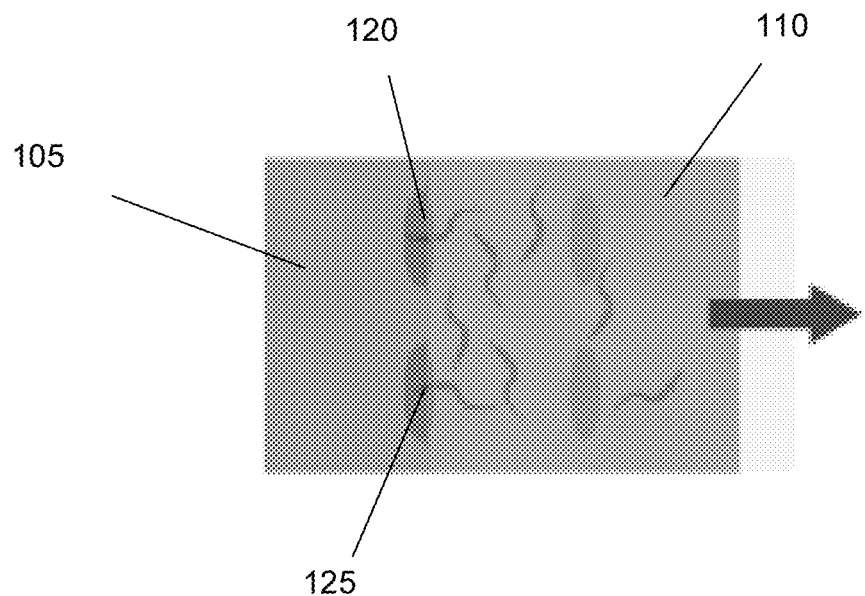

FIG. 5B provides an illustration of the substrate during the method of manipulating a biological substance in an open fluidic array device, in accordance with an exemplary embodiment of the present disclosure.

Figure 6A:
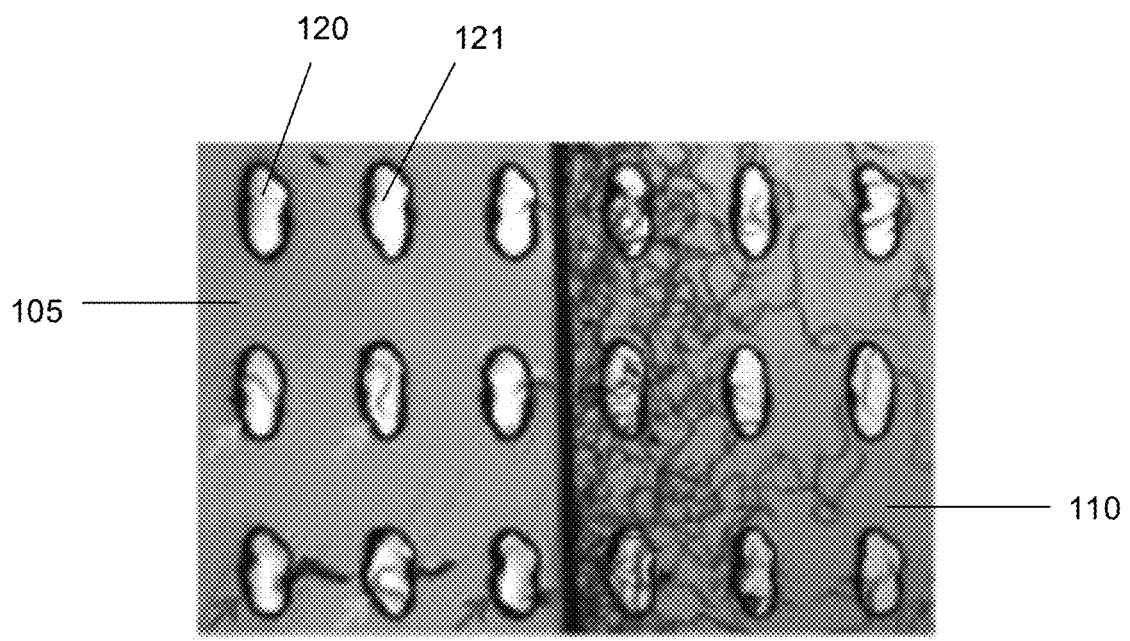

FIG. 6A provides an image of the substrate during the method of manipulating a biological substance in an open fluidic array device, in accordance with an exemplary embodiment of the present disclosure.

Figure 6B:
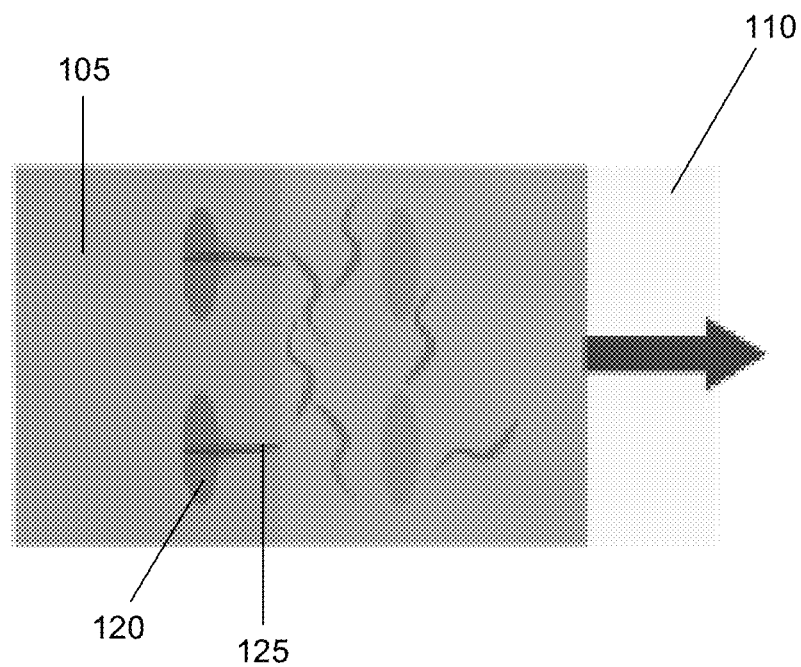

FIG. 6B provides an illustration of the substrate during the method of manipulating a biological substance in an open fluidic array device, in accordance with an exemplary embodiment of the present disclosure.

Figure 7A:
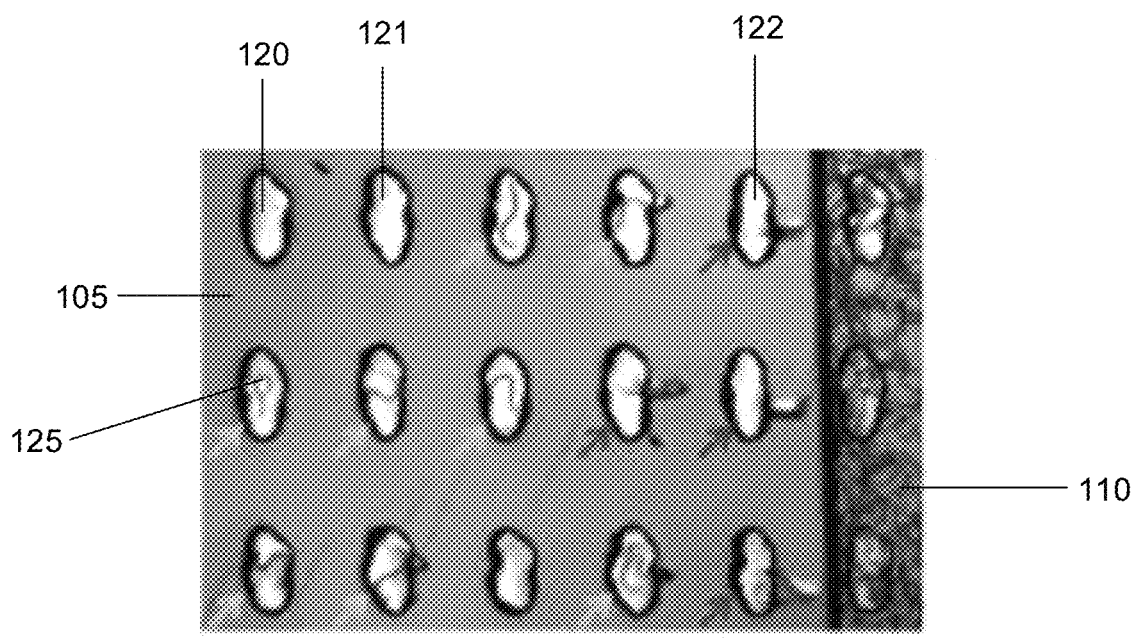

FIG. 7A provides an image of the substrate during the method of manipulating a biological substance in an open fluidic array device, in accordance with an exemplary embodiment of the present disclosure.

Figure 7B:
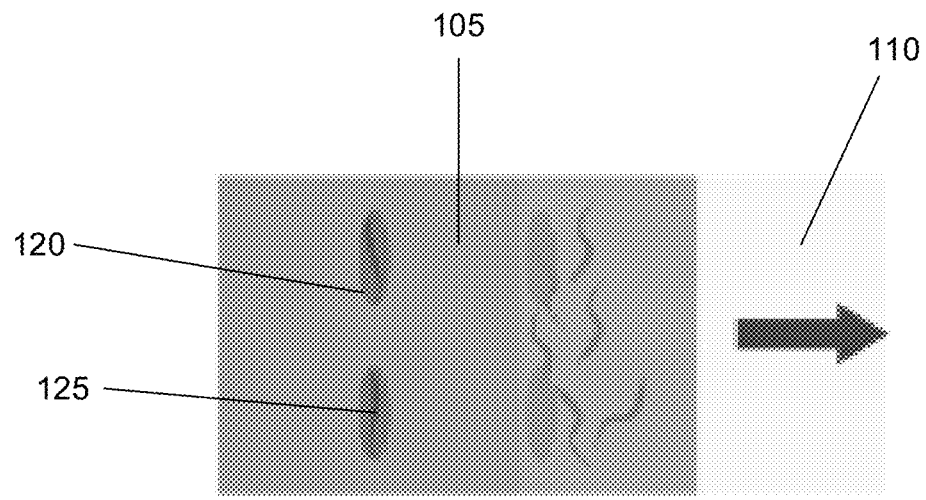

FIG. 7B provides an illustration of the substrate during the method of manipulating a biological substance in an open fluidic array device, in accordance with an exemplary embodiment of the present disclosure.

Figure 8A:
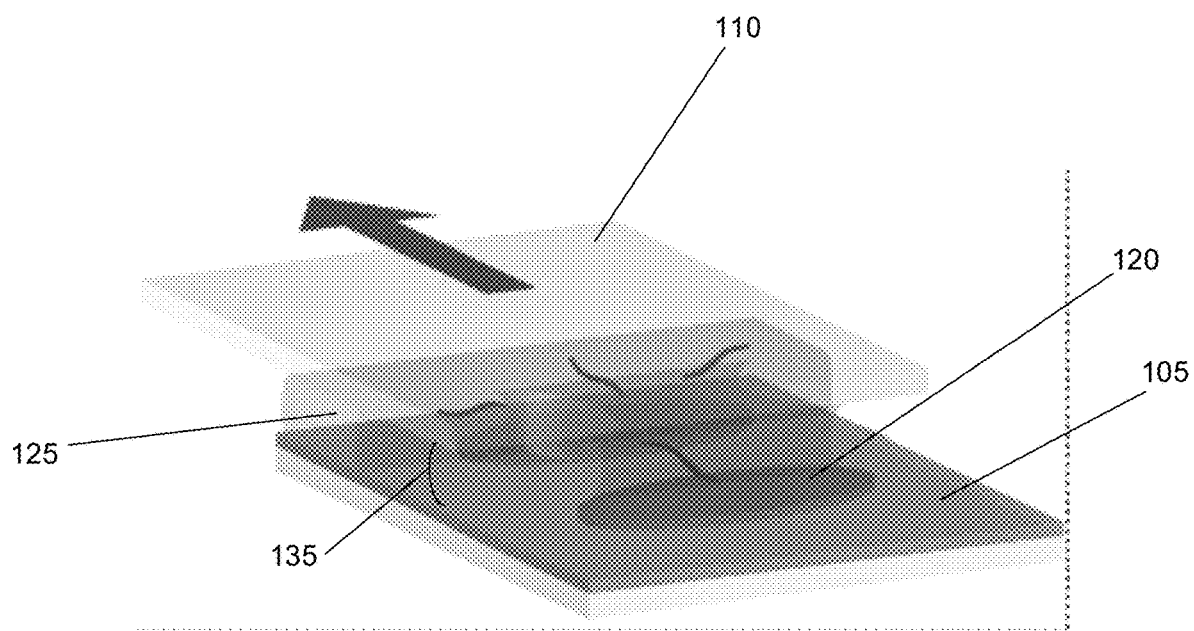

FIG. 8A provides an illustration of a close-up view of moving the applicator along the top surface of the substrate while maintaining the space between the top surface of the substrate and the bottom surface of the applicator, in accordance with an exemplary embodiment of the present disclosure.

Figure 8B:
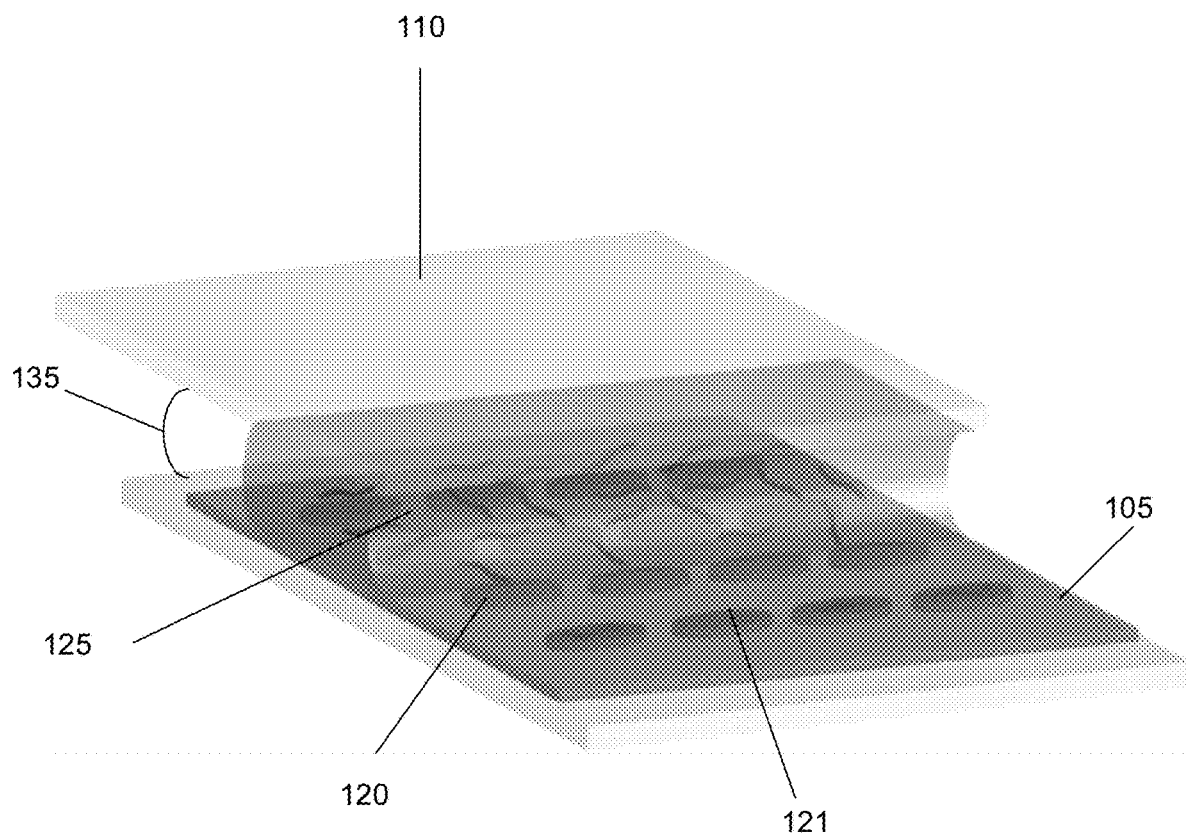

FIG. 8B provides an illustration of moving the applicator along the top surface of the substrate while maintaining the space between the top surface of the substrate and the bottom surface of the applicator, in accordance with an exemplary embodiment of the present disclosure.

Figure 9A:
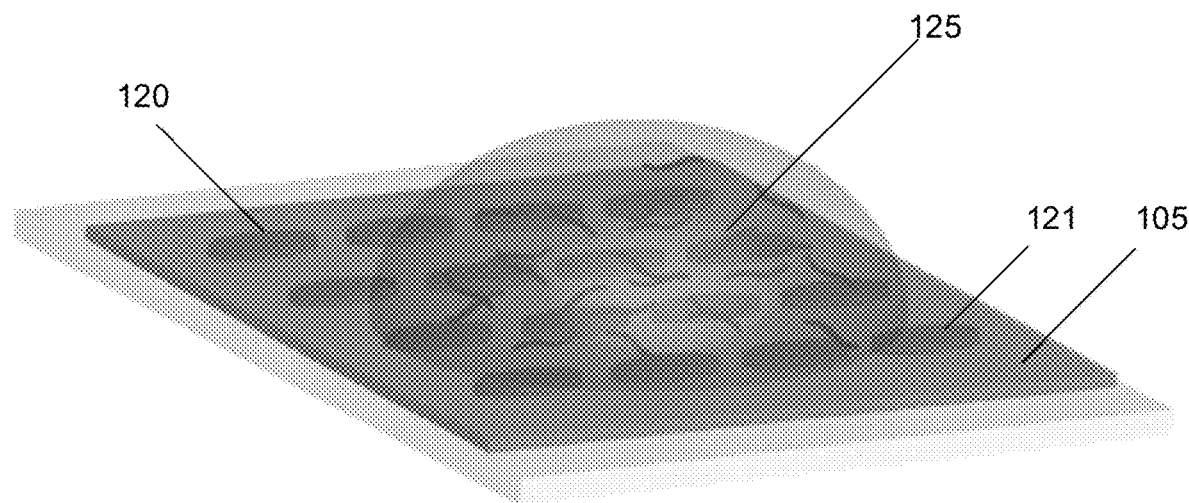

FIG. 9A provides an illustration of the substrate with biological substance, in accordance with an exemplary embodiment of the present disclosure.

Figure 9B:
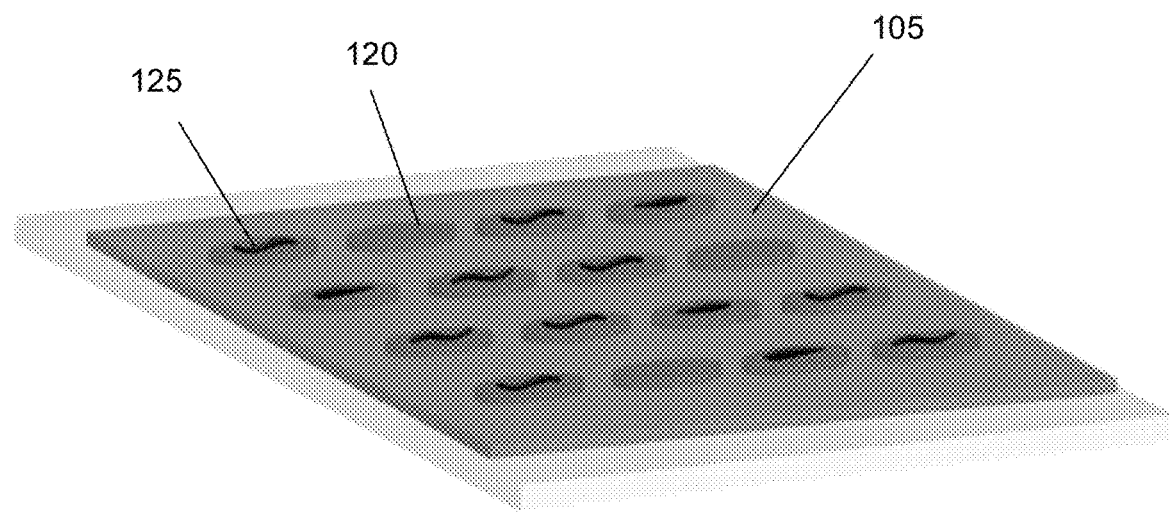

FIG. 9B provides an illustration of the substrate with biological substance after using the method of manipulating a biological substance in an open fluidic array device, in accordance with an exemplary embodiment of the present disclosure.

Figure 10:
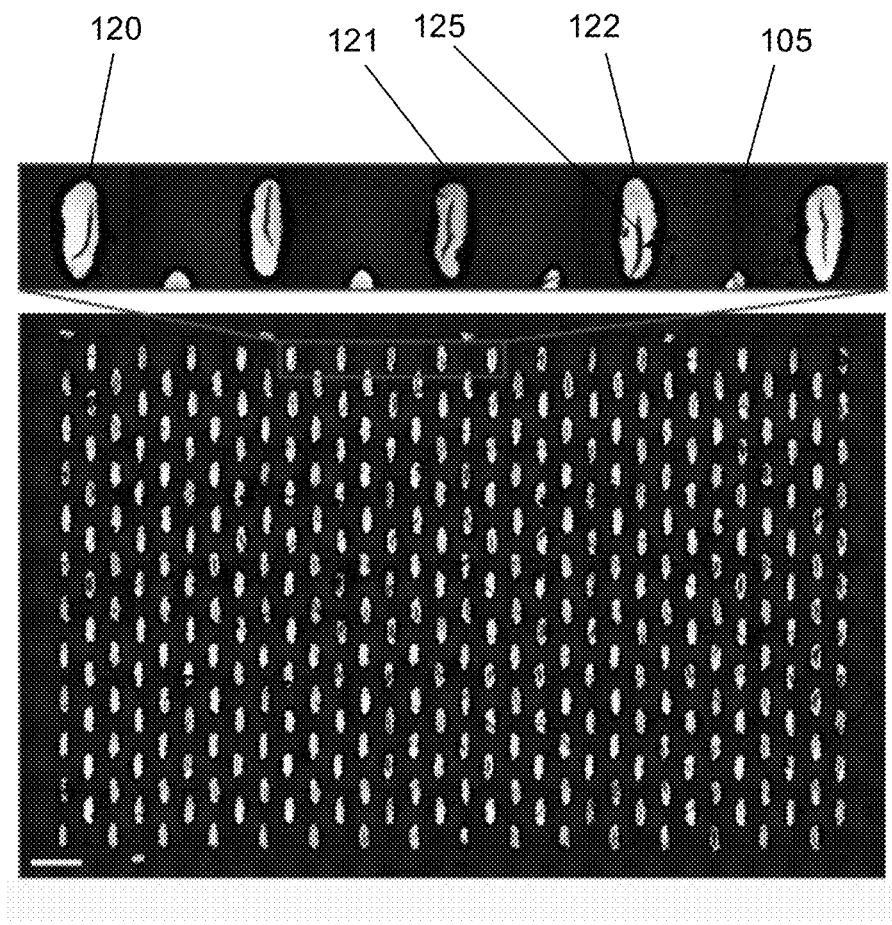

FIG. 10 provides an image of an open fluidic array device after applying the biological substance to the plurality of wells with an applicator, in accordance with an exemplary embodiment of the present disclosure.

Figure 11:
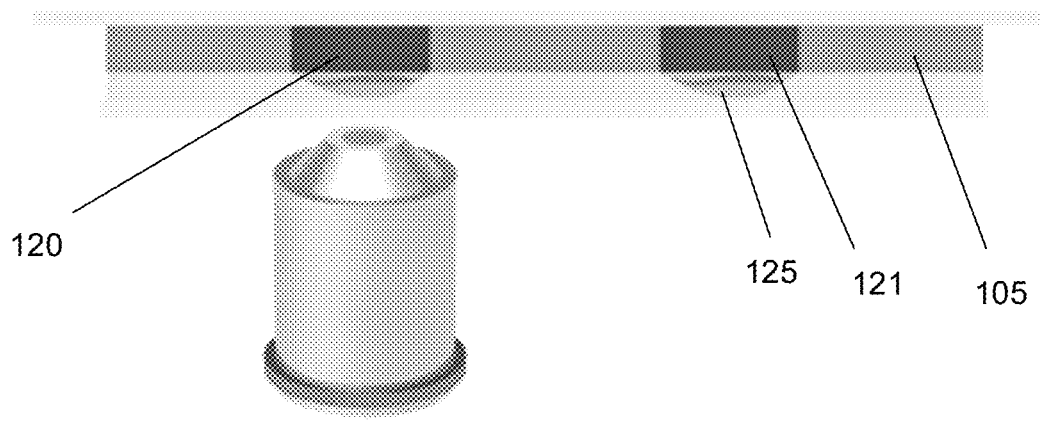

FIG. 11 provides an illustration of covering an open fluidic array device with a coverslip or other similar materials known in the art and inverting the position of the open fluidic array device, in accordance with an exemplary embodiment of the present disclosure.

Figure 12:
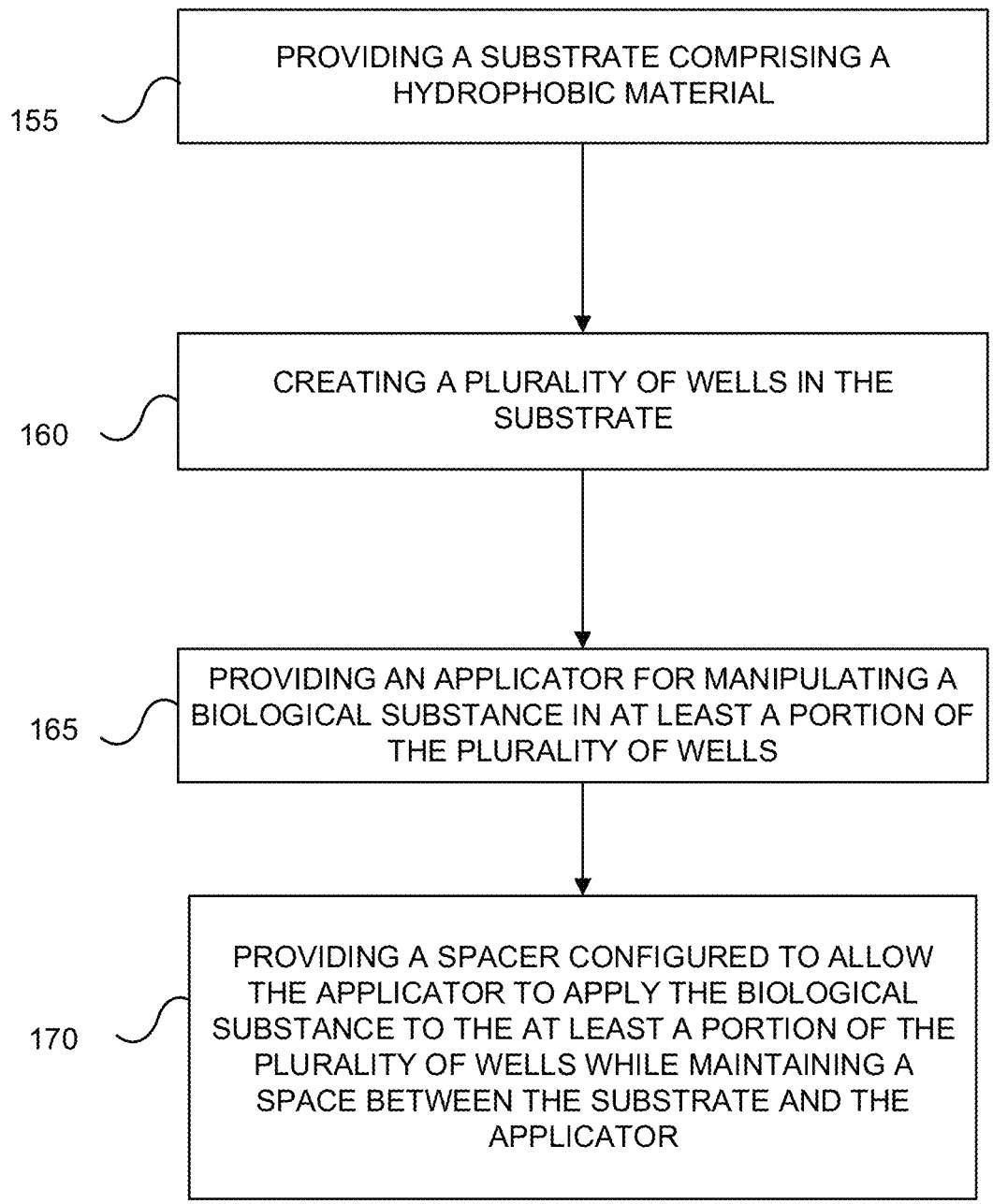

FIG. 12 provides a flow diagram outlining the method of making an open fluidic array device, in accordance with an exemplary embodiment of the present disclosure.

Figure 13:
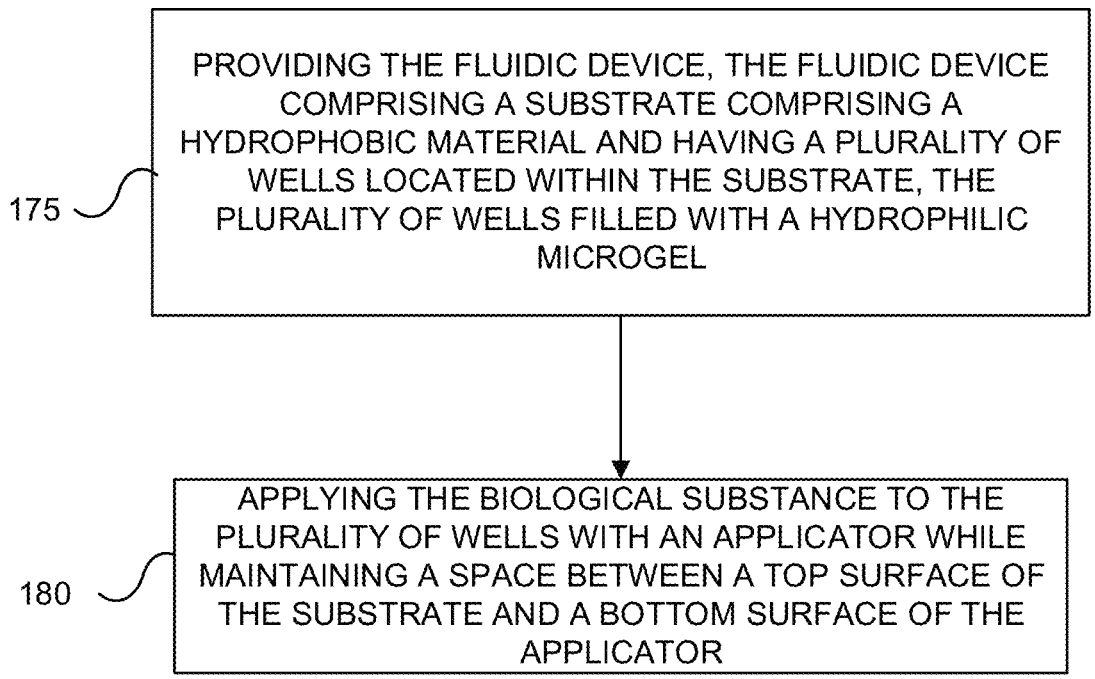

FIG. 13 provides a flow diagram outlining the method of manipulating a biological substance in an open fluidic array device, in accordance with an exemplary embodiment of the present disclosure.

DETAILED DESCRIPTION

To facilitate an understanding of the principles and features of the present disclosure, various illustrative embodiments are explained below. The components, steps, and materials described hereinafter as making up various elements of the embodiments disclosed herein are intended to be illustrative and not restrictive. Many suitable components, steps, and materials that would perform the same or similar functions as the components, steps, and materials described herein are intended to be embraced within the scope of the disclosure. Such other components, steps, and materials not described herein can include, but are not limited to, similar components or steps that are developed after development of the embodiments disclosed herein.

As discussed above, conventional open-surface microfluidic techniques use either manual loading or stochastic sample sedimentation by gravity and mostly work only with static single cells. Embodiments of the present disclosure, however, are not so limited. Rather, embodiments of the present disclosure can be applied to a wide range of samples, including, but not limited to, artificial systems such as vesicles, macromolecules, and even highly motile multi-cellular organisms with larger length scale. Embodiments of the present disclosure can not only work with highly motile multi-cellular organisms but can also enable rapid sample loading and high-percentage sample isolation simultaneously. To address this challenge while retaining the benefit of open microfluidics, embodiments of the present disclosure can take advantage of fast interfacial dynamics to isolate biological substances. The fluidic devices and methods disclosed herein can control the local capillary pressures at the interface between a biological substance of micro-swimmer suspension and the fluidic device substrate. The methods of using the fluidic devices disclosed herein can drive a rapid movement of local contact lines, which dominate over the active locomotion of micro-swimmers, and hence can achieve open-surface sample isolation. The methods of using the fluidic device disclosed herein can be fast, simple, and robust without any external connections, pumps, or controllers. The methods can handle a wide range of biological substances, including both static and moving samples, from single cells, cell aggregates, to even small living model organisms. Additionally, the fluidic devices disclosed herein can be easily manufactured using common and readily available materials and, importantly, can be fabricated outside a cleanroom using machines that cost only a few hundred dollars. General users with no engineering expertise can master the disclosed methods of using the fluidic devices within minutes. The open accessibility of the fluidic device can allow for individual interrogation of biological substances. It is with respect to these and other considerations that the various embodiments described below are presented.

Figure 1B:
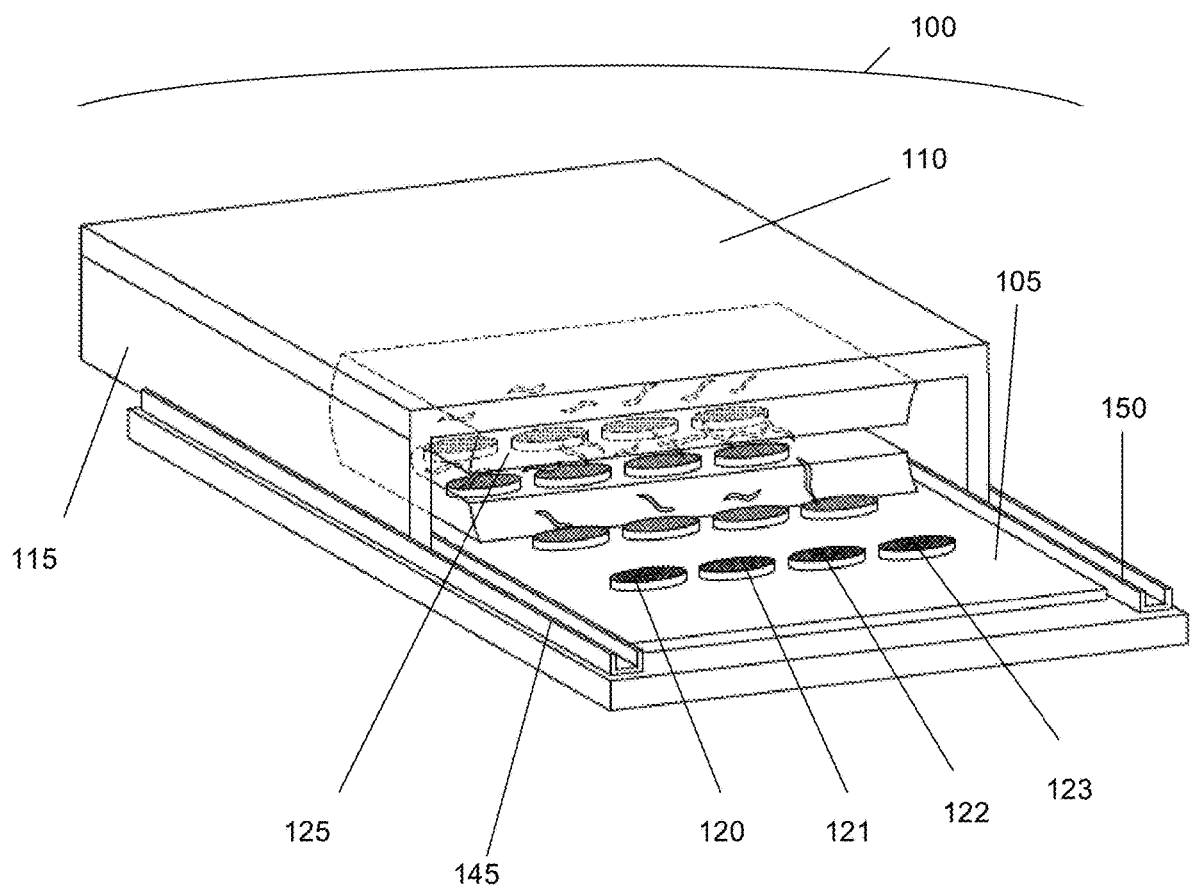

As shown in FIG. 1A and FIG. 1B, an exemplary embodiment of the present disclosure provides a fluidic device 100. The fluidic device 100 can comprise a substrate 105, an applicator 110, and a spacer 115. The substrate 105 can comprise a plurality of wells 120-123. The applicator 110 can be used for manipulating a biological substance 125 in at least a portion of the plurality of wells 120-123. The spacer 115 can be positioned between the substrate 105 and the applicator 110. The spacer 115 can be configured to allow the applicator 110 to apply the biological substance 125 to at least a portion of the plurality of wells 120-123 while maintaining a space between the substrate 105 and the applicator 110.

The substrate 105 can be many different materials known in the art. In some embodiments, the substrate 105 can comprise a hydrophobic material. The hydrophobic material can be many hydrophobic materials known in the art, including, but not limited to, Kapton tape, polydimethylsiloxane (PDMS) membrane, polystyrene (PS) film, cyclic olefin copolymer (CoC) film, and any plastic and hydrogel materials that have proper surface wettability, combinations thereof, and the like. The hydrophobic material can define the boundaries of the plurality of wells 120-123.

Figure 2A:
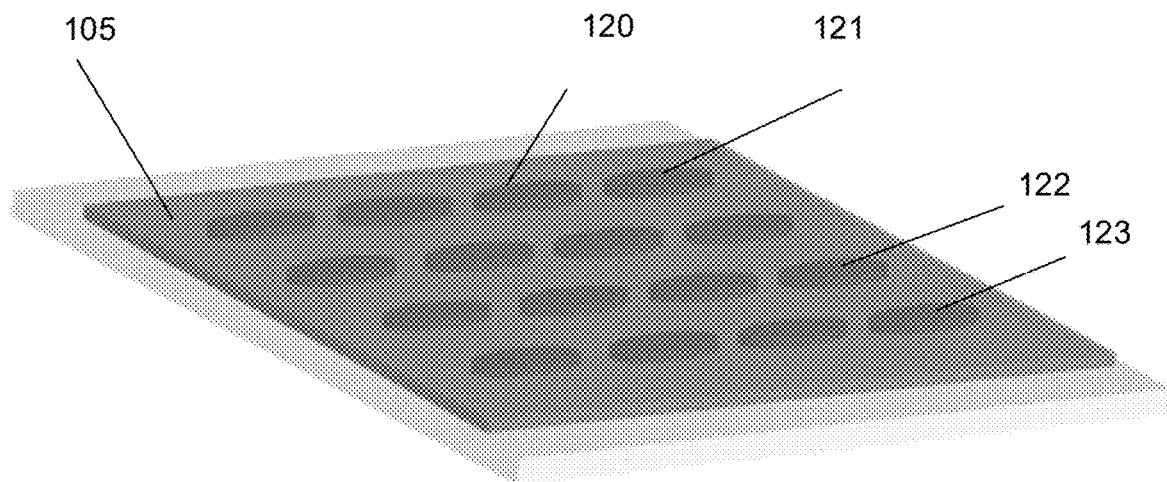
Figure 2B:
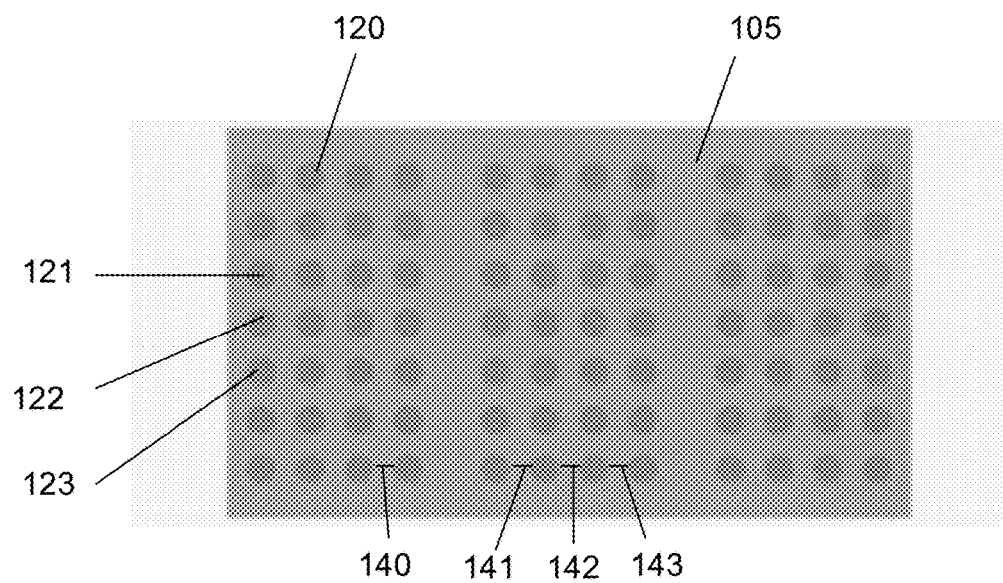

As shown in FIG. 2A and FIG. 2B, the substrate 105 can take many different shapes in accordance with various embodiments. In some embodiments, the substrate 105 can have a generally planar shape. In some embodiments, the substrate 105 can be non-planar or textured. In some embodiments, the substrate 105 can be heterogeneous.

Figure 3A:
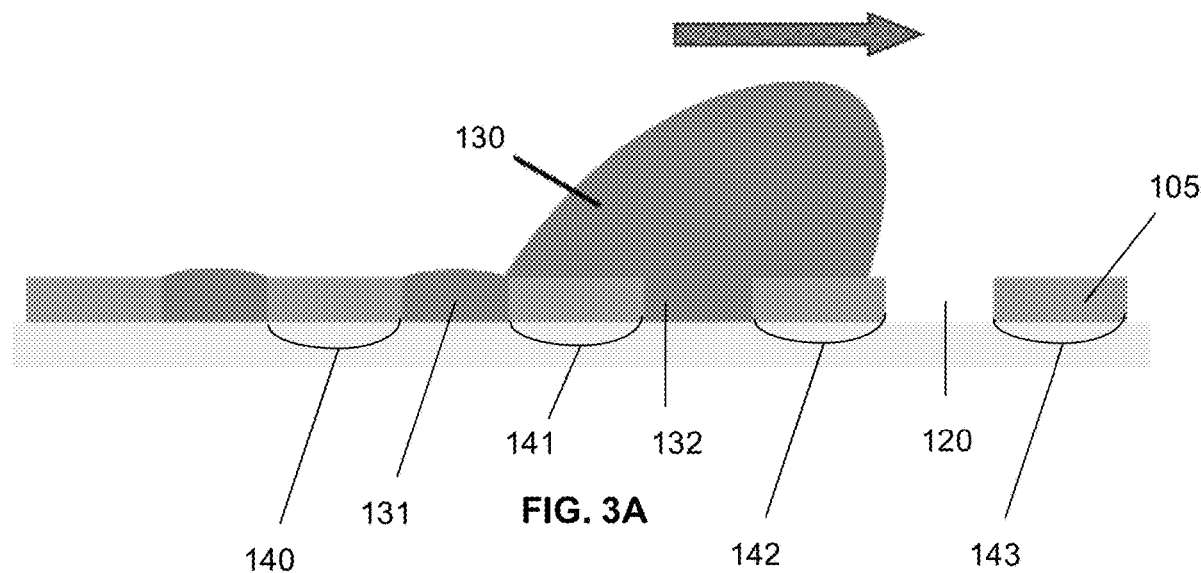

As shown in FIG. 3A, the plurality of wells 120-123 can be at least partially filled with a hydrophilic microgel 130-132. The hydrophilic microgel 130 can be many hydrophilic materials known in the art, including, but not limited to, polyethylene glycol (PEG)-based micro gel pads, sol-gel such as Pluoronic, agarose gel, Matrigel, gelatin methacryloyl (GelMA) hydrogels, combinations thereof, and the like.

Figure 3B:
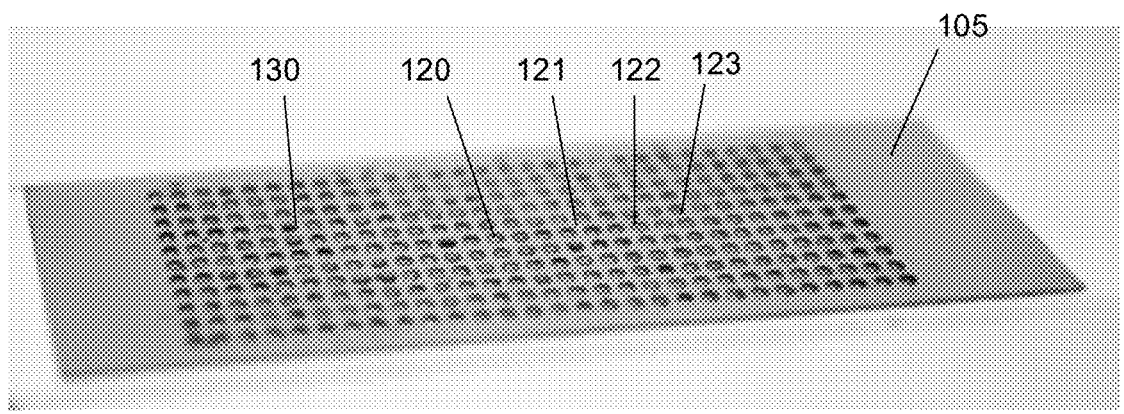

As shown in FIG. 3B, FIG. 8A, and FIG. 8B, the plurality of wells 120-123 can be spaced apart in the substrate 105 such that the following equation is satisfied, $$\frac{h}{d} < \left(1 - \frac{\cos\theta_{substrate}}{\cos\theta_{microgel}}\right)$$

wherein h can be a height 135 of the space between the substrate 105 and the applicator 110, d can be a distance 140-143 between adjacent wells in the plurality of wells 120-123, $\theta_{microgel}$ can be a receding contact angle of the hydrophilic microgel 130, and $\theta_{substrate}$ can be a receding contact angle of the hydrophobic material. In some embodiments, the distance 140-143 can be defined as the length of the space between two adjacent hydrophilic microgels 130-132.

The biological substance 125 can be many different materials known in the art. In some embodiments, the biological substance 125 can comprise an aqueous solution. The aqueous solution can be many aqueous solutions known in the art, including, but not limited to, pharmacological agents, anesthetics, cell culture media, physiological buffers, PBS solution, or small molecule drug solution, combinations thereof, and the like. In some embodiments, the biological substance 125 can be many biological entities known in the art, including, but not limited to, cells, cell aggregates, micro-organisms, multi-cellular organisms, *C. elegans*, *D. melanogaster* embryos, *D. rerio* embryos, stem cell aggregates, embryoid bodies, organoids, cancer spheroids, engineered tissues, or single cell model systems, including, but not limited to *E. coli* and yeast, combinations thereof, and the like.

As shown in FIG. 1B, in some embodiments, the spacer 115 can be an independent component. In some embodiments, the spacer 115 can be located on or attached to many different parts of the fluidic device 100, including, but not limited to, on the substrate 105 and/or on the applicator 110, combinations thereof, and the like. For example, in some embodiments, the spacer 115 can be attached to the substrate 105, in some embodiments the spacer 115 can be attached to the applicator 110, and in some embodiments a portion of the spacer 115 can be attached to the substrate 105 and another portion of the spacer 115 can be attached to the applicator 110. In some embodiments, the spacer 115 can comprise of a first rail 145 and a second rail 150. The first rail 145 can extend along at least a portion of a top surface of the substrate. The second rail 150 can extend along at least a portion of the top surface of the substrate. The first rail 145 can substantially be parallel to the second rail 150.

As shown in FIG. 12, an exemplary embodiment in the form of a flow diagram of the present disclosure provides a method of making the fluidic device 100. The method can comprise: providing 155 a substrate 105 comprising a hydrophobic material; creating 160 a plurality of wells 120-123 in the substrate 105; providing 165 an applicator 110 for manipulating a biological substance 125 in at least a portion of the plurality of wells 120-123; and providing 170 a spacer 115 configured to allow the applicator 110 to apply the biological substance 125 to the at least a portion of the plurality of wells 120-123 while maintaining a space between the substrate 105 and the applicator 110.

Figure 4A:
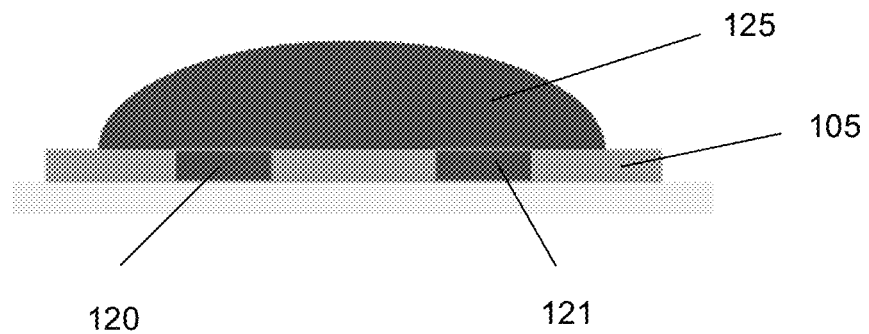
Figure 4B:
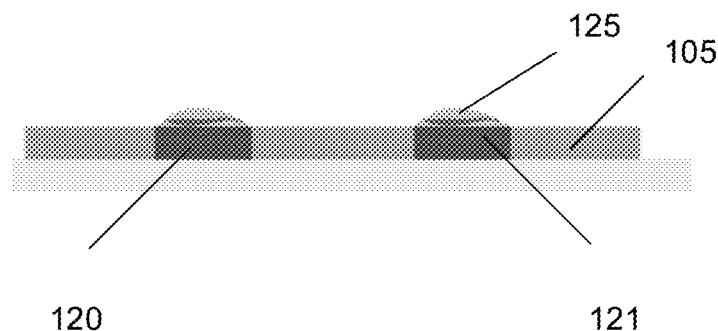

As shown in FIG. 4A and FIG. 9A, to apply the biological substance 125 the biological substance 125 can be placed on the substrate 105 before moving the applicator 110.

As shown in FIG. 3A, the method can further include filling the plurality of wells 120-123 with a hydrophilic microgel 130. In some embodiments, filling the plurality of wells 120-123 with a hydrophilic microgel 130 can comprise a dewetting process.

The method can further include gelating, including, but not limited to, crosslinking the hydrophilic microgel 130. In some embodiments, the crosslinking can comprise exposing the hydrophilic microgel 130 to ultraviolet light. In some embodiments, depending on the hydrophilic microgel 130 material, the hydrophilic microgel can be formed by temperature changes or by waiting for time to pass.

In some embodiments, the substrate 105 can be coated with bio-compatible silicone oil or similar materials known in the art to prevent evaporation.

In some embodiments, creating 160 the plurality of wells 120-123 can result in the plurality of wells 120-123 being spaced apart in the substrate 105 such that the following equation is satisfied, $$\frac{h}{d} < \left(1 - \frac{\cos\theta_{substrate}}{\cos\theta_{microgel}}\right)$$

wherein h can be a height 135 of the space between the substrate 105 and the applicator 110, d can be a distance 140-143 between adjacent wells in the plurality of wells, $\theta_{microgel}$ can be a receding contact angle of the hydrophilic microgel, and $\theta_{substrate}$ can be a receding contact angle of the hydrophobic material. In some embodiments, the distance 140-143 can be defined as the length of the space between two adjacent hydrophilic microgels 130-132.

Creating 160 the plurality of wells 120-123 can be achieved in many different ways known in the art, including, but not limited to, laser cutting the substrate 105, micro machining the substrate 105, or blade cutting the substrate 105, combinations thereof, and the like.

In some embodiments, providing 170 the spacer 115 can comprise at least one of providing the spacer 115 on the applicator 110 and providing the spacer on the substrate 105, combinations thereof, and the like. In some embodiments, providing 170 the spacer 115 can comprise of the spacer 115 being an independent component, unattached to the substrate 105 and the applicator 110.

As shown in FIG. 13, an exemplary embodiment in the form of a flow diagram of the present disclosure provides a method of manipulating a biological substance in a fluidic device 100. The method can comprise: providing 175 the fluidic device 100; and applying 180 the biological substance 125 to the plurality of wells 120-123 with an applicator 110. The fluidic device 100 can comprise a substrate 105 and a plurality of wells 120-123. The substrate 105 can comprise a hydrophobic material. The plurality of wells 120-123 can be located within the substrate 105. The plurality of wells 120-123 can be filled with a hydrophilic microgel 130. The biological substance 125 to the plurality of wells 120-123 can be applied with an applicator 110 while maintaining a space between a top surface of the substrate 105 and a bottom surface of the applicator 110.

In some embodiments, applying 180 the biological substance 125 to the plurality of wells 120-123 can comprise moving the applicator 110 along the top surface of the substrate 105 while maintaining the space between the top surface of the substrate 105 and the bottom surface of the applicator 110.

In some embodiments, the space between the top surface of the substrate 105 and the bottom surface of the applicator 110 can be maintained by a spacer 115 positioned between the top surface of the substrate 105 and the bottom surface of the applicator 110.

In some embodiments, the space between the top surface of the substrate 105 and the bottom surface of the applicator 110 can satisfy the following equation, $$\frac{h}{d} < \left(1 - \frac{\cos\theta_{substrate}}{\cos\theta_{microgel}}\right)$$

wherein h can be a height 135 of the space between the top surface of the substrate 105 and the bottom surface of the applicator 110, d can be a distance 140-143 between adjacent wells in the plurality of wells 120-123, $\theta_{microgel}$ can be a receding contact angle of the hydrophilic microgel 130-132, and $\theta_{substrate}$ can be a receding contact angle of the hydrophobic material. In some embodiments, the distance 140-143 can be defined as the length of the space between two adjacent hydrophilic microgels 130-132.

As shown in FIG. 8, in some embodiments, moving the applicator 110 along the top surface of the substrate 105 can comprise moving the applicator 110 along the top surface of the substrate 105 at a predetermined speed. In some embodiments, the predetermined speed can be calculated according to the following equation, $$t_c/t_{sliding} = Ca \ 3 \ l_g/\alpha h$$

wherein $t_c$ can be a local meniscus collapsing timescale, $t_{sliding}$ can be a biological substance 125 sliding timescale, Ca can be a capillary number, $l_g$ can be a length of wells in the plurality of wells 120-123, and α can be calculated according to the following equation, $$\alpha = (\cos\theta_{microgel} - \cos\theta_{substrate}) - \frac{h}{d}\cos\theta_{microgel}$$

wherein h can be a height 135 of the space between the top surface of the substrate 105 and the bottom surface of the applicator 110, d can be a distance 140-143 between adjacent wells in the plurality of wells 120-123, $\theta_{microgel}$ can be a receding contact angle of the hydrophilic microgel 130-132, and $\theta_{substrate}$ can be a receding contact angle of the hydrophobic material.

As shown in FIG. 11, in some embodiments, the method can further comprise of covering the fluidic device 100 with a coverslip or other similar materials known in the art and shifting the position of the fluidic device 100 for imaging purposes.

The following examples further illustrate aspects of the present disclosure. However, they are in no way a limitation of the teachings or disclosure of the present disclosure as set forth herein.

EXAMPLES

The fluidic device and methods can be used for high-throughput imaging, culture, and selection of biological samples, including, but not limited to, model multi-cellular systems, wildlife microorganisms, active multicellular micro-swimmers, and multiplexed combinatorial drug and compound screening.

In a second example, the invention can be used to enable applications for screening of antibiotic and anthelmintic drug development or therapeutic methods of human diseases, and can serve as a low-cost, easy-access tool for studying fundamental neuroscience, immunology, cell and developmental biology, and regenerative medicine with a wide range of biological systems.

In a third example, the fluidic device and methods can be used to perform high-throughput phenotypic and genetic analysis of model biosystems, including, but not limited to protein expression, cell development, synapse formation, and transcription analysis.

In a fourth example, the fluidic device and methods can be used for drug screening, using phenotypes of the model organism such as cell morphology or behavior as readouts.

In a fifth example, drugs with different compositions and concentrations can be applied to modify the hydrophilic microgel, and the effect of these drugs can be evaluated by the resulted behavior or morphology changes of the biological substance cultured on the fluidic device.

In a sixth example, the fluidic device and methods in our invention allows for multiplexed chemical modification of the individual microenvironment in which isolated model systems are cultured. It hence allows for combinatorial and scalable screening of a large library of drugs.

In a seventh example, the fluidic device and methods can be used for studying, observing, and naming tumor spheroids.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:

1. A fluidic device comprising:
   a substrate comprising wells;
   an applicator for applying a biological substance to at least a portion of the wells; and
   a spacer disposed on the substrate and comprising:
      a first rail extending along at least a portion of a top surface of the substrate; and
      a second rail extending along at least a portion of the top surface of the substrate, the second rail substantially parallel to the first rail;
   wherein the spacer is configured to enable the applicator to apply the biological substance to the at least a portion of the wells while maintaining a space between the substrate and the applicator.

2. The fluidic device of claim 1, wherein one or more of the wells are at least partially filled with a hydrophilic microgel.

3. The fluidic device of claim 2, wherein the substrate comprises a hydrophobic material defining boundaries of the wells.

4. The fluidic device of claim 3, wherein the wells are spaced apart in the substrate such that the following equation is satisfied:

$$\frac{h}{d} < \left(1 - \frac{\cos\theta_{substrate}}{\cos\theta_{microgel}}\right);$$

wherein:
   h is a height of the maintained space between the substrate and the applicator;
   d is a distance between adjacent wells;
   $\theta_{microgel}$ is a receding contact angle of the hydrophilic microgel; and
   $\theta_{substrate}$ is a receding contact angle of the hydrophobic material.

5. A method comprising:
   applying, with an applicator, a biological substance in at least a portion of wells formed in a substrate comprising a hydrophobic material; and
   maintaining, with a spacer, a space between the substrate and the applicator during the applying;
   wherein the spacer is disposed on the substrate and comprises:
      a first rail extending along at least a portion of a top surface of the substrate; and
      a second rail extending along at least a portion of the top surface of the substrate, the second rail substantially parallel to the first rail.

6. The method of claim 5, further comprising at least partially filling the wells with a hydrophilic microgel.

7. The method of claim 6, wherein the filling comprises a dewetting process.

8. The method of claim 6, further comprising crosslinking the hydrophilic microgel.

9. The method of claim 8, wherein the crosslinking comprises exposing the hydrophilic microgel to ultraviolet light.

10. The method of claim 6, wherein the wells are spaced apart in the substrate such that the following equation is satisfied:

$$\frac{h}{d} < \left(1 - \frac{\cos\theta_{substrate}}{\cos\theta_{microgel}}\right);$$

wherein:
   h is a height of the maintained space between the substrate and the applicator;
   d is a distance between adjacent wells;
   $\theta_{microgel}$ is a receding contact angle of the hydrophilic microgel; and
   $\theta_{substrate}$ is a receding contact angle of the hydrophobic material.

11. The method of claim 5, further comprising creating the wells by at least one of laser cutting the substrate, micro machining the substrate, or blade cutting the substrate.

12. A method comprising:
   moving an applicator along a top surface of a substrate while maintaining a space between the top surface of the substrate and a bottom surface of the applicator; and
   applying, with the moving applicator, a biological substance in wells at least partially filled with a hydrophilic microgel, the wells formed in the substrate, the substrate comprising a hydrophobic material;
   wherein the moving comprises moving the applicator along the top surface of the substrate at a predetermined speed, the predetermined speed calculated according to the following equation:

$$t_c/t_{sliding} = C\alpha 3\ l_g/\alpha h;$$

wherein;
   $t_c$ is a local meniscus collapsing timescale;
   $t_{sliding}$ is a biological substance sliding timescale;
   $C\alpha$ is a capillary number;
   $l_g$ is a length of the wells; and
   $\alpha$ is calculated according to the following equation:

$$\alpha = (\cos\theta_{microgel} - \cos\theta_{substrate}) - \frac{h}{d}\cos\theta_{microgel}$$

wherein;
   h is a height of the maintained space between the top surface of the substrate and the bottom surface of the applicator;
   d is a distance between adjacent wells;
   $\theta_{microgel}$ is a receding contact angle of the hydrophilic microgel; and
   $\theta_{substrate}$ is a receding contact angle of the hydrophobic material.

13. The method of claim 12, wherein the wells are spaced in the substrate such that the following equation is satisfied:

$$\frac{h}{d} < \left(1 - \frac{\cos\theta_{substrate}}{\cos\theta_{microgel}}\right)$$

14. The method of claim 12, wherein the maintaining the space comprises maintaining the space by a spacer positioned between the top surface of the substrate and the bottom surface of the applicator.

* * * * *